United States Patent
Lima et al.

(10) Patent No.: US 7,937,159 B2
(45) Date of Patent: *May 3, 2011

(54) APPARATUS, SYSTEM AND METHOD FOR THERAPEUTIC TREATMENT OF OBSTRUCTIVE SLEEP APNEA

(75) Inventors: Marcelo G. Lima, San Diego, CA (US); Stanley R. Craig, Jr., Westport, MA (US)

(73) Assignee: ImThera Medical Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/752,931

(22) Filed: Apr. 1, 2010

(65) Prior Publication Data
US 2010/0198306 A1    Aug. 5, 2010

Related U.S. Application Data

(63) Continuation of application No. 11/707,053, filed on Feb. 16, 2007, now Pat. No. 7,725,195.

(60) Provisional application No. 60/774,039, filed on Feb. 16, 2006, provisional application No. 60/774,040, filed on Feb. 16, 2006, provisional application No. 60/774,041, filed on Feb. 16, 2006.

(51) Int. Cl.
A61N 1/05    (2006.01)
(52) U.S. Cl. ......................................................... 607/60
(58) Field of Classification Search ...................... 607/60
See application file for complete search history.

(56) References Cited

U.S. PATENT DOCUMENTS

| | | |
|---|---|---|
| 4,424,812 A | 1/1984 | Lenick |
| 4,602,624 A | 7/1986 | Naples et al. |
| 5,094,242 A | 3/1992 | Gleason et al. |
| 5,095,905 A | 3/1992 | Klepinski |
| 5,123,425 A | 6/1992 | Shannon, Jr. et al. |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,190,053 A | 3/1993 | Meer |
| 5,211,173 A | 5/1993 | Kallok et al. |
| 5,215,082 A | 6/1993 | Kallok et al. |
| 5,233,983 A | 8/1993 | Markowitz |
| 5,281,219 A | 1/1994 | Kallok |
| 5,300,094 A | 4/1994 | Kallok et al. |

(Continued)

FOREIGN PATENT DOCUMENTS

EP    2116274 A2    11/2009
(Continued)

OTHER PUBLICATIONS

International Search Report from International Application No. PCT/US2010/036070, dated Jul. 21, 2010.

(Continued)

*Primary Examiner* — Eric D. Bertram
(74) *Attorney, Agent, or Firm* — Morgan, Lewis & Bockius LLP

(57) ABSTRACT

An implantable neurostimulator for treating obstructive sleep apnea comprises an implant configured to at least partially surround a Hypoglossal nerve (HGN) and a plurality of electrodes each attached to the implant. Each electrode configured to contact the HGN and electrically stimulate one or more regions or groups of the HGN.

36 Claims, 7 Drawing Sheets

U.S. PATENT DOCUMENTS

| | | | |
|---|---|---|---|
| 5,344,438 A | 9/1994 | Testerman et al. | |
| 5,483,969 A | 1/1996 | Testerman et al. | |
| 5,522,862 A | 6/1996 | Testerman et al. | |
| 5,540,731 A | 7/1996 | Testerman | |
| 5,540,732 A | 7/1996 | Testerman | |
| 5,540,733 A | 7/1996 | Testerman et al. | |
| 5,545,201 A | 8/1996 | Helland et al. | |
| 5,546,952 A | 8/1996 | Erickson | |
| 5,591,216 A | 1/1997 | Testerman et al. | |
| 5,713,922 A | 2/1998 | King | |
| 5,771,891 A | 6/1998 | Gozani | |
| 5,837,006 A | 11/1998 | Ocel et al. | |
| 5,871,512 A | 2/1999 | Hemming et al. | |
| 5,988,171 A | 11/1999 | Sohn et al. | |
| 6,021,352 A | 2/2000 | Christopherson et al. | |
| 6,051,017 A * | 4/2000 | Loeb et al. | 607/1 |
| 6,132,384 A | 10/2000 | Christopherson et al. | |
| 6,175,767 B1 | 1/2001 | Doyle, Sr. | |
| 6,212,435 B1 | 4/2001 | Lattner et al. | |
| 6,240,316 B1 * | 5/2001 | Richmond et al. | 607/42 |
| 6,251,126 B1 | 6/2001 | Ottenhoff et al. | |
| 6,266,560 B1 | 7/2001 | Zhang et al. | |
| 6,269,269 B1 | 7/2001 | Ottenhoff et al. | |
| 6,345,202 B2 | 2/2002 | Richmond et al. | |
| 6,408,852 B2 | 6/2002 | Tielemans | |
| 6,409,676 B2 | 6/2002 | Ruton et al. | |
| 6,415,174 B1 | 7/2002 | Bebehani et al. | |
| 6,427,689 B1 | 8/2002 | Estes et al. | |
| 6,432,956 B1 | 8/2002 | Dement et al. | |
| 6,454,724 B1 | 9/2002 | Greene | |
| 6,456,866 B1 | 9/2002 | Tyler et al. | |
| 6,475,156 B1 | 11/2002 | Vega | |
| 6,488,634 B1 | 12/2002 | Rapoport et al. | |
| 6,516,802 B2 | 2/2003 | Hansen et al. | |
| 6,516,805 B1 | 2/2003 | Thornton | |
| 6,529,752 B2 | 3/2003 | Krausman et al. | |
| 6,536,439 B1 | 3/2003 | Palmisano | |
| 6,555,564 B1 | 4/2003 | Radulovacki et al. | |
| 6,572,543 B1 | 6/2003 | Christopherson et al. | |
| 6,574,507 B1 | 6/2003 | Bonnet | |
| 6,580,944 B1 | 6/2003 | Katz et al. | |
| 6,586,478 B2 | 7/2003 | Ackman et al. | |
| 6,587,725 B1 | 7/2003 | Durand et al. | |
| 6,594,370 B1 | 7/2003 | Anderson | |
| 6,595,215 B2 | 7/2003 | Wood | |
| 6,613,779 B2 | 9/2003 | Mondadori et al. | |
| 6,629,527 B1 | 10/2003 | Estes et al. | |
| 6,635,021 B1 | 10/2003 | Sullivan et al. | |
| 6,636,767 B1 | 10/2003 | Knudson et al. | |
| 6,641,542 B2 | 11/2003 | Cho et al. | |
| 6,658,301 B2 | 12/2003 | Loeb et al. | |
| 6,666,830 B1 | 12/2003 | Lehrman et al. | |
| 6,671,907 B1 | 1/2004 | Zuberi | |
| 6,705,315 B2 | 3/2004 | Sullivan et al. | |
| 6,727,242 B2 | 4/2004 | Radulovacki et al. | |
| 6,729,335 B1 | 5/2004 | Halstrom | |
| 6,731,984 B2 | 5/2004 | Cho et al. | |
| 6,752,766 B2 | 6/2004 | Kowallik et al. | |
| 6,761,167 B1 | 7/2004 | Nadjafizadeh et al. | |
| 6,761,168 B1 | 7/2004 | Nadjafizadeh et al. | |
| 6,766,802 B1 | 7/2004 | Keropian | |
| 6,770,022 B2 | 8/2004 | Mechlenburg et al. | |
| 6,770,037 B2 | 8/2004 | Sullivan et al. | |
| 6,773,404 B2 | 8/2004 | Poezevera et al. | |
| 6,776,162 B2 | 8/2004 | Wood | |
| 6,788,975 B1 | 9/2004 | Whitehurst et al. | |
| 6,793,629 B2 | 9/2004 | Rapoport et al. | |
| 6,807,967 B2 | 10/2004 | Wood | |
| 6,811,538 B2 | 11/2004 | Westbrook et al. | |
| 6,814,074 B1 | 11/2004 | Nadjafizadeh et al. | |
| 6,818,665 B2 | 11/2004 | Wennerholm et al. | |
| 6,835,740 B2 | 12/2004 | Rubin et al. | |
| 6,857,149 B2 | 2/2005 | Hoggatt et al. | |
| 6,878,121 B2 | 4/2005 | Krausman et al. | |
| 6,881,192 B1 | 4/2005 | Park | |
| 6,884,596 B2 | 4/2005 | Civelli et al. | |
| 6,890,306 B2 | 5/2005 | Poezevera | |
| 6,893,405 B2 | 5/2005 | Kumar et al. | |
| 6,901,292 B2 | 5/2005 | Hrdlicka et al. | |
| 6,904,320 B2 | 6/2005 | Park et al. | |
| 6,918,394 B2 | 7/2005 | Matsuda et al. | |
| 6,928,324 B2 | 8/2005 | Park et al. | |
| 6,964,641 B2 | 11/2005 | Cho et al. | |
| 6,999,819 B2 | 2/2006 | Swoyer et al. | |
| 7,003,352 B1 | 2/2006 | Whitehurst | |
| 7,092,763 B1 | 8/2006 | Griffith et al. | |
| 7,184,836 B1 | 2/2007 | Meadows et al. | |
| 7,245,971 B2 | 7/2007 | Park et al. | |
| 7,570,997 B2 | 8/2009 | Lovett et al. | |
| 7,644,714 B2 | 1/2010 | Atkinson et al. | |
| 7,725,195 B2 | 5/2010 | Lima et al. | |
| 2001/0000346 A1 | 4/2001 | Ruton et al. | |
| 2001/0001125 A1 | 5/2001 | Schulman et al. | |
| 2001/0010010 A1 | 7/2001 | Richmond et al. | |
| 2001/0015204 A1 | 8/2001 | Hansen et al. | |
| 2001/0018557 A1 | 8/2001 | Lynn et al. | |
| 2001/0027793 A1 | 10/2001 | Tielemans | |
| 2001/0041719 A1 | 11/2001 | Mondadori et al. | |
| 2001/0046988 A1 | 11/2001 | Iglehart | |
| 2002/0007127 A1 | 1/2002 | Sullivan et al. | |
| 2002/0015740 A1 | 2/2002 | Ackman et al. | |
| 2002/0037533 A1 | 3/2002 | Civelli et al. | |
| 2002/0049479 A1 | 4/2002 | Pitts | |
| 2002/0059935 A1 | 5/2002 | Wood | |
| 2002/0086870 A1 | 7/2002 | Radulovacki et al. | |
| 2002/0092527 A1 | 7/2002 | Wood | |
| 2002/0095076 A1 | 7/2002 | Krausman et al. | |
| 2002/0099033 A1 | 7/2002 | Meyer et al. | |
| 2002/0100477 A1 | 8/2002 | Sullivan et al. | |
| 2002/0124848 A1 | 9/2002 | Sullivan et al. | |
| 2002/0124849 A1 | 9/2002 | Billette De Villemeur et al. | |
| 2002/0144684 A1 | 10/2002 | Moone | |
| 2002/0144685 A1 | 10/2002 | Ivanovich et al. | |
| 2002/0165246 A1 | 11/2002 | Holman | |
| 2002/0165462 A1 | 11/2002 | Wesbrook et al. | |
| 2002/0169384 A1 | 11/2002 | Kowallik et al. | |
| 2002/0173707 A1 | 11/2002 | Lynn et al. | |
| 2002/0175821 A1 | 11/2002 | Ruppel | |
| 2002/0183306 A1 | 12/2002 | Howard, Jr. | |
| 2002/0193697 A1 | 12/2002 | Cho et al. | |
| 2002/0193839 A1 | 12/2002 | Cho et al. | |
| 2003/0004423 A1 | 1/2003 | Lavie et al. | |
| 2003/0015198 A1 | 1/2003 | Heeke et al. | |
| 2003/0021772 A1 | 1/2003 | Birkmayer | |
| 2003/0053956 A1 | 3/2003 | Hofmann | |
| 2003/0055346 A1 | 3/2003 | Rapoport et al. | |
| 2003/0055348 A1 | 3/2003 | Chazal et al. | |
| 2003/0056785 A1 | 3/2003 | Narihiko et al. | |
| 2003/0083241 A1 | 5/2003 | Young | |
| 2003/0093131 A1 | 5/2003 | Loeb et al. | |
| 2003/0130266 A1 | 7/2003 | Radulovacki et al. | |
| 2003/0130589 A1 | 7/2003 | Poezevera | |
| 2003/0139680 A1 | 7/2003 | Sheldon | |
| 2003/0139691 A1 | 7/2003 | Kumar et al. | |
| 2003/0139789 A1 | 7/2003 | Tvinnereim et al. | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0167018 A1 | 9/2003 | Wyckoff | |
| 2003/0172462 A1 | 9/2003 | Hoggatt et al. | |
| 2003/0176788 A1 | 9/2003 | Crutchfield et al. | |
| 2003/0181958 A1 | 9/2003 | Dobak, III | |
| 2003/0183227 A1 | 10/2003 | Klemperer | |
| 2003/0195140 A1 | 10/2003 | Ackman et al. | |
| 2003/0195571 A1 | 10/2003 | Burnes et al. | |
| 2003/0204213 A1 | 10/2003 | Jensen et al. | |
| 2003/0216789 A1 | 11/2003 | Deem et al. | |
| 2003/0232839 A1 | 12/2003 | Hangauer et al. | |
| 2003/0235313 A1 | 12/2003 | Kurzweil et al. | |
| 2003/0236228 A1 | 12/2003 | Radulovacki et al. | |
| 2004/0002516 A1 | 1/2004 | Mondadori et al. | |
| 2004/0002742 A1 | 1/2004 | Florio | |
| 2004/0006339 A1 | 1/2004 | Underwood et al. | |
| 2004/0006375 A1 | 1/2004 | Poezevera | |
| 2004/0016433 A1 | 1/2004 | Estes et al. | |

| | | |
|---|---|---|
| 2004/0020493 A1 | 2/2004 | Wood |
| 2004/0025885 A1 | 2/2004 | Payne, Jr. |
| 2004/0029869 A1 | 2/2004 | Iglehart, III |
| 2004/0030224 A1 | 2/2004 | Sotos et al. |
| 2004/0055597 A1 | 3/2004 | Virr et al. |
| 2004/0059240 A1 | 3/2004 | Cho et al. |
| 2004/0082519 A1 | 4/2004 | Hedner et al. |
| 2004/0087866 A1 | 5/2004 | Bowman et al. |
| 2004/0087878 A1 | 5/2004 | Krausman et al. |
| 2004/0097871 A1 | 5/2004 | Yerushalmy |
| 2004/0111041 A1 | 6/2004 | Ni et al. |
| 2004/0127572 A1 | 7/2004 | Carley et al. |
| 2004/0134491 A1 | 7/2004 | Pflueger et al. |
| 2004/0138719 A1 | 7/2004 | Cho et al. |
| 2004/0144391 A1 | 7/2004 | Brady et al. |
| 2004/0146873 A1 | 7/2004 | Ptacek et al. |
| 2004/0157813 A1 | 8/2004 | Wennerholm et al. |
| 2004/0176695 A1 | 9/2004 | Poezevara |
| 2004/0176809 A1 | 9/2004 | Cho et al. |
| 2004/0186523 A1 | 9/2004 | Florio |
| 2004/0187873 A1 | 9/2004 | Brown |
| 2004/0200472 A1 | 10/2004 | Gold |
| 2004/0210261 A1 | 10/2004 | King et al. |
| 2004/0215095 A1 | 10/2004 | Lee et al. |
| 2004/0225226 A1 | 11/2004 | Lehrman et al. |
| 2004/0235807 A1 | 11/2004 | Weinrich et al. |
| 2004/0254493 A1 | 12/2004 | Chervin et al. |
| 2005/0008587 A1 | 1/2005 | Schulz et al. |
| 2005/0015117 A1 | 1/2005 | Gerber |
| 2005/0016536 A1 | 1/2005 | Rapoport et al. |
| 2005/0020930 A1 | 1/2005 | Salisbury et al. |
| 2005/0022821 A1 | 2/2005 | Jeppesen |
| 2005/0027207 A1 | 2/2005 | Westbrook et al. |
| 2005/0031688 A1 | 2/2005 | Ayala |
| 2005/0034730 A1 | 2/2005 | Wood |
| 2005/0038013 A1 | 2/2005 | Gold |
| 2005/0039757 A1 | 2/2005 | Wood |
| 2005/0042589 A1 | 2/2005 | Hatlestad et al. |
| 2005/0043645 A1 | 2/2005 | Ono et al. |
| 2005/0043652 A1 | 2/2005 | Lovett et al. |
| 2005/0045190 A1 | 3/2005 | Bennett |
| 2005/0048538 A1 | 3/2005 | Mignot et al. |
| 2005/0061315 A1 | 3/2005 | Lee et al. |
| 2005/0061320 A1 | 3/2005 | Lee et al. |
| 2005/0061326 A1 | 3/2005 | Payne, Jr. |
| 2005/0076906 A1 | 4/2005 | Johnson |
| 2005/0080461 A1 | 4/2005 | Stahmann et al. |
| 2005/0081854 A1 | 4/2005 | Nadjafizadeh et al. |
| 2005/0085738 A1 | 4/2005 | Stahmann et al. |
| 2005/0085874 A1 | 4/2005 | Davis et al. |
| 2005/0090871 A1 | 4/2005 | Cho et al. |
| 2005/0101833 A1 | 5/2005 | Hsu et al. |
| 2005/0113646 A1 | 5/2005 | Sotos et al. |
| 2005/0113710 A1 | 5/2005 | Stahmann et al. |
| 2005/0119285 A1 | 6/2005 | Matos et al. |
| 2005/0126574 A1 | 6/2005 | Wood |
| 2005/0133026 A1 | 6/2005 | Seleznev et al. |
| 2005/0143617 A1 | 6/2005 | Auphan |
| 2005/0148893 A1 | 7/2005 | Misczynski et al. |
| 2005/0148897 A1 | 7/2005 | Cho et al. |
| 2005/0149146 A1 | 7/2005 | Boveja et al. |
| 2005/0150504 A1 | 7/2005 | Heeke et al. |
| 2005/0215947 A1 | 9/2005 | Heruth et al. |
| 2005/0240253 A1 | 10/2005 | Tyler et al. |
| 2005/0258242 A1 | 11/2005 | Zarembo |
| 2005/0277999 A1 | 12/2005 | Strother et al. |
| 2006/0095078 A1 | 5/2006 | Tronnes |
| 2006/0095088 A1 | 5/2006 | De Ridder |
| 2006/0122653 A1 | 6/2006 | Bradley et al. |
| 2006/0149337 A1 | 7/2006 | John |
| 2006/0212096 A1* | 9/2006 | Stevenson ............. 607/60 |
| 2006/0224211 A1 | 10/2006 | Durand et al. |
| 2007/0021794 A1 | 1/2007 | Kieval et al. |
| 2007/0043398 A1 | 2/2007 | Ternes et al. |
| 2007/0055308 A1 | 3/2007 | Haller et al. |
| 2007/0066997 A1 | 3/2007 | He et al. |
| 2007/0100399 A1 | 5/2007 | Parramon et al. |
| 2007/0100411 A1 | 5/2007 | Bonde |
| 2007/0129768 A1 | 6/2007 | He et al. |
| 2007/0150006 A1 | 6/2007 | Libbus et al. |
| 2007/0150022 A1 | 6/2007 | Ujhazy et al. |
| 2007/0173893 A1 | 7/2007 | Pitts |
| 2007/0233204 A1 | 10/2007 | Lima et al. |
| 2007/0255366 A1 | 11/2007 | Gerber et al. |
| 2007/0255367 A1 | 11/2007 | Gerber et al. |
| 2008/0021506 A1 | 1/2008 | Grocela et al. |
| 2008/0039904 A1 | 2/2008 | Bulkes et al. |
| 2008/0039916 A1 | 2/2008 | Colliou et al. |
| 2008/0091246 A1 | 4/2008 | Carey et al. |
| 2008/0097554 A1 | 4/2008 | Payne et al. |
| 2008/0103407 A1 | 5/2008 | Bolea et al. |
| 2008/0103544 A1 | 5/2008 | Weiner |
| 2008/0103545 A1 | 5/2008 | Bolea et al. |
| 2008/0109047 A1 | 5/2008 | Pless |
| 2008/0114230 A1 | 5/2008 | Addis |
| 2008/0139913 A1 | 6/2008 | Schulman |
| 2008/0172109 A1 | 7/2008 | Rahman et al. |
| 2008/0288025 A1 | 11/2008 | Peterson |
| 2009/0118796 A1 | 5/2009 | Chen et al. |
| 2009/0210042 A1 | 8/2009 | Kowalczewski |
| 2009/0270904 A1 | 10/2009 | Birk et al. |
| 2010/0139667 A1 | 6/2010 | Atkinson et al. |

FOREIGN PATENT DOCUMENTS

| | | |
|---|---|---|
| WO | 9900058 A1 | 1/1999 |
| WO | 02087433 A1 | 11/2002 |
| WO | 2007092330 A1 | 8/2007 |
| WO | 2007098200 A2 | 8/2007 |
| WO | 2007098202 A2 | 8/2007 |
| WO | 2007117232 A1 | 10/2007 |
| WO | 2007140584 A1 | 12/2007 |
| WO | 2008005903 A2 | 1/2008 |
| WO | 2008039921 A2 | 4/2008 |
| WO | 2008046190 A1 | 4/2008 |
| WO | 2008048471 A2 | 4/2008 |
| WO | 2008049199 A1 | 5/2008 |
| WO | 2009048580 A1 | 4/2009 |
| WO | 2009048581 A1 | 4/2009 |
| WO | 2009140636 A2 | 11/2009 |
| WO | 2010039853 A1 | 4/2010 |
| WO | 2010059839 A2 | 5/2010 |

OTHER PUBLICATIONS

Written Opinion of the International Search Authority Application No. PCT/US2010/036070, dated Jul. 21, 2010.
Office Action from U.S. Appl. No. 11/707,104 dated Jun. 21, 2010.
Non-Final Office Action mailed Nov. 5, 2010 in connection with U.S. Appl. No. 12/752,931.
International Search Report for PCT/US2009/59374 dated Dec. 3, 2009.
Gilliam, Edwin E. and Goldberg, Stephen J., Contractile Properties of the Tongue Muscles: Effects of Hypoglossal Nerve and Extracellular Motoneuron Stimulation in Rat, Journal of Neurophysiology, vol. 74, No. 2, Aug. 1995, pp. 547-555.
Nagai, et al., Effect of Aging on Tongue Protrusion Forces in Rats; Dysphagia (2008) 23:116-121.
Pae, Eung-Kwon et al., Short-Term Electrical Stimulation Alters Tongue Muscle Fibre Type Composition; Archives of Oral Biology, vol. 52, Issue 6 (Jun. 2007) 544-551.
Davis, et al., Development of the Bion® Microstimulator for Treatment in Obstructive Sleep Apnea, Alfred Mann Foundation, Valencia, California, Jul. 1-5, 2003, IFESS.
Sutlive et al., Whole-Muscle and Motor-Un It Contractile Properties of the Styloglossus Muscle in Rat, The American Physiological Society, 1999, pp. 584-592.
Sutlive et al., Contractile Properties of the Tongue's Genioglossus Muscle and Motor Units in the Rat, Genioglossus Muscle Properties, Muscle & Nerve, Mar. 2000 pp. 416-425.
Smith et al., Phenotype and Contractile Properties of Mammalian Tongue Muscles Innervated by the Hypoglossal Nerve, Respiratory Physiology and Neurobiology 147 (Feb. 23, 2005) 253-262.
Sawczuk et al., Neural Control of Tongue Movement With Respect to Respiration and Swallowing, Crit Rev Oral Viol Med, 12(I):18-37 (2001).

International Search Report for PCT/US2007/04512 dated Nov. 29, 2007.
International Search Report for PCT/US2007/04514 dated Nov. 29, 2007.
International Search Report for PCT/US2008/011598 dated Dec. 12, 2008.
International Search Report for PCT/US2008/011599 dated Dec. 12, 2008.
Final Office Action mailed Nov. 4, 2010 in connection with U.S. Appl. No. 11/707,104.
George S. Goding, Jr., et al., "Relief of Upper Airway Obstruction With Hypoglossal Nerve Stimulation in the Canin," The Laryngoscope, Feb. 1998, 108:2, pp. 162-169.
Frederick G. Weiss, "Implications of Silicon Monolithic RFICs for Medical Instrumentation and Telemetry," IEEE, 1998, pp. 195-204.
Philip R. Troyk, "Injectable Electronic Identification, Monitoring, and Stimulation Systems," Annu. Rev. Biomed. Eng. 1999, 01:177-209.
Mesut Sahin, et al., "Closed-Loop Stimulation of Hypoglossal Nerve in a Dog Model of Upper Airway Obstruction," IEEE Transactions on Biomedical Engineering, vol. 47, No. 7, pp. 919-925, Jul. 2000.
Alan R. Schwartz, et al., "Therapeutic Electrical Stimulation of the Hypoglossal Nerve in Obstructive Sleep Apnea," Arch Otolaryngol Head Neck Surg/vol. 127, Oct. 2001, pp. 1216-1223.

P.B. Yoo et al., "Selective Stimulation of the Hypoglossal Nerve with multi-Contact Cuff Electrode," 2001 IEEE, pp. 1309-1312.
David W. Eisele, M.D., et al., "Tongue neuromuscular and direct hypoglossal nerve stimulation for obstructive sleep apnea," Otolaryngol Clin N Am 36 (2003) 501-510.
W.H. Tran, et al., "Development of Asynchronous, Intralingual Electrical Stimulation to Treat Obstructive Sleep Apnea," 2003 IEEE, pp. 375-378.
Jingtao Huang, et al., "Activation Patterns of the Tongue Muscles With Selective Stimulation of the Hypoglossal Nerve," 2004 IEEE, pp. 4275-4278.
Michael Arndt, "Rewiring the Body," Business Week, Mar. 7, 2005, pp. 74-82.
Paul B. Yoo, et al., "A Neural Prosthesis for Obstructive Sleep Apnea," 2005, IEEE, pp. 5254-5256.
Melanie Wells, "The Sleep Racket Who's making big bucks off your insomnia?" Forbes, Feb. 27, 2006, pp. 80-88.
Fairbanks, David W., M.D.; Fairbanks, David N.F., M.D.; Neurostimulation for Obstructive Sleep Apnea: Investigations; ENT Journal; Jan. 19993; pp. 52-57; vol. 72, No. 1; International Pub. Group; Cleveland, OH.

* cited by examiner

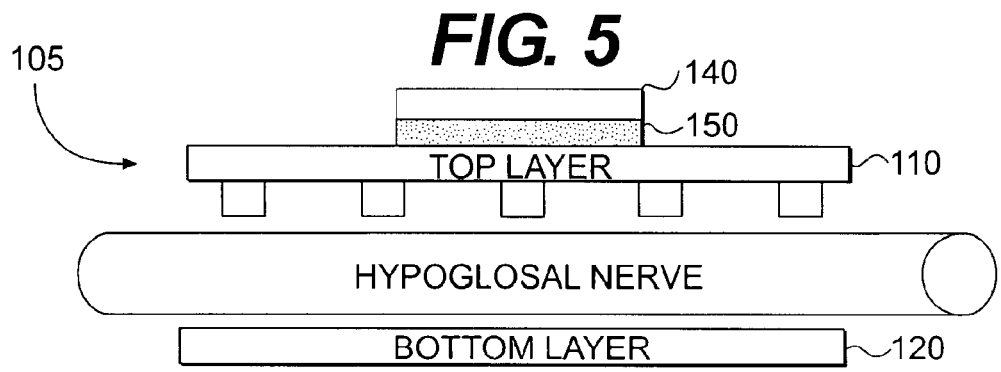
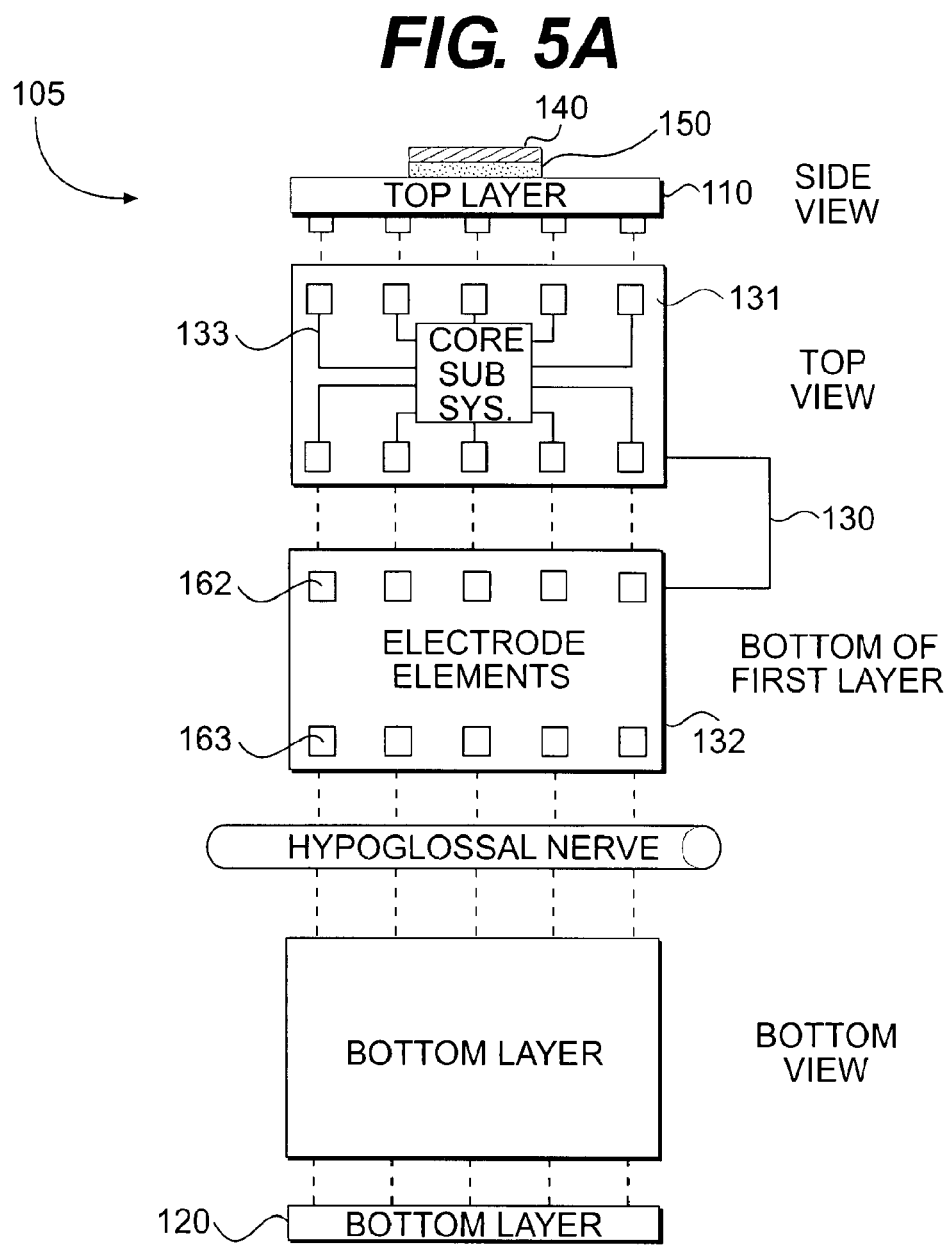

APPARATUS, SYSTEM AND METHOD FOR THERAPEUTIC TREATMENT OF OBSTRUCTIVE SLEEP APNEA

RELATED APPLICATIONS

This application is a continuation of U.S. patent application Ser. No. 11/707,053, now U.S. Pat. No. 7,725,195, filed on Feb. 16, 2007 which claims priority to U.S. Provisional Applications 60/774,039, 60/774,040, and 60/774,041 filed on Feb. 16, 2006, all of which are expressly incorporated herein by reference in their entirety.

FIELD OF THE INVENTION

The present invention relates to an apparatus, system, and method for implantable therapeutic treatment of obstructive sleep apnea.

BACKGROUND OF THE INVENTION

Sleep apnea is a physiological condition affecting millions of people worldwide. It is described as an iterated failure to respire properly during sleep. Those affected by sleep apnea stop breathing during sleep numerous times during the night. There are two types of sleep apnea, generally described in medical literature as central sleep apnea and obstructive sleep apnea. Central sleep apnea is a failure of the nervous system to produce proper signals for excitation of the muscles involved with respiration. Obstructive sleep apnea (OSA) is cause by physical obstruction of the upper airway channel (UAW).

Obstruction of the upper airway is associated with a depression of the respiratory system caused by a loss of tone of the oropharyngeal muscles involved in maintaining UAW patency. As those muscles lose tone, the tongue and soft tissue of the upper airway collapse, blocking the upper airway channel. Blockage of the upper airway prevents air from flowing into the lungs. This creates a decrease in blood oxygen level, which in turn increases blood pressure and heart dilation. This causes a reflexive forced opening of the UAW until the patient regains normal patency, followed by normal respiration until the next apneic event. These reflexes briefly arouse the patient from sleep (microarousals).

Current treatment options range from non-invasive approaches such as continuous positive applied pressure (CPAP) to more invasive surgical procedures such as uvulopalatopharyngoplasty (UPPP) and tracheostomy. In both cases patient acceptance and therapy compliance is well below desired levels, rendering the current solutions ineffective as a long term solution-for therapeutic treatment of OSA.

Implants are a promising alternative to these forms of treatment. Pharyngeal dilation via hypoglossal nerve (XII) stimulation has been shown to be an effective treatment method for OSA. The nerves are stimulated using an implanted electrode. In particular, the medial XII nerve branch (i.e., in. genioglossus), has demonstrated significant reductions in UAW airflow resistance (i.e., increased pharyngeal caliber).

Reduced UAW airflow resistance, however, does not address the issue of UAW compliance (i.e., decreased UAW stiffness), another critical factor involved with maintaining patency. To this end, co-activation of both the lateral XII nerve branches (which innervate the hyoglossus (HG) and styloglossus (SG) muscles) and the medial nerve branch has shown that the added effects of the HG (tongue retraction and depression) and the SG (retraction and elevation of lateral aspect of tongue) result in an increased maximum rate of airflow and mechanical stability of the UAW.

While coarse (non-selective) stimulation has shown improvement to the AHI (Apnea+Hypopnea Index) the therapeutic effects of coarse stimulation are inconclusive. Selective stimulation of the functional branches is more effective, since each branch-controlled muscle affects different functions and locations of the upper airway. For example, activation of the GH muscle moves the hyoid bone in the anterosuperior direction (towards the tip of the chin). This causes dilation of the pharynx, but at a point along the upper airway that is more caudal (below) to the base of the tongue. In contrast, activation of the HG dilates the oropharynx (the most commonly identified point of collapse, where the tongue and soft palate meet) by causing tongue protrusion. Finally, the tongue retractor muscles (HG and SG) do not themselves generate therapeutic effects, but they have been shown to improve upper airway stability when co-activated with the HG muscle.

While electrical stimulation of the hypoglossal nerve (HGN) has been experimentally shown to remove obstructions in the UAW, current implementation methods require accurate detection of an obstruction, selective stimulation of the correct tongue muscles, and a coupling of the detection and stimulation components. Additionally, attempts at selective stimulation have to date required multiple implants with multiple power sources, and the scope of therapeutic efficacy has been limited. A need therefore exists for an apparatus and method for programmable and/or selective neural stimulation of multiple implants or contact excitation combinations using a single controller power source.

SUMMARY OF THE INVENTION

The present invention relates to an apparatus, system, and method for selective and programmable implants for the therapeutic treatment of obstructive sleep apnea.

In one embodiment, an implantable RFID-enabled microelectronic neurostimulator system for treating obstructive sleep apnea includes an external subsystem and an internal subsystem. In this embodiment, the internal subsystem includes an implant having a top and a bottom layer, the bottom layer serving as an attachment mechanism such that the bottom layer of the implant encompasses the HGN and attaches to the top layer of the implant. A printed circuit board (PCB) is attached to the top layer of the implant, with the PCB having first and second opposing sides. A neural interface attaches to the second side of the PCB. A core subsystem (CSS) attaches to the first side of the PCB and electrically connects to the neural interface. An internal radio frequency (RF) interface attaches to the first side of the PCB and is electrically connected to the CSS. The power may be supplied by RF energy emitted from the external subsystem.

In some embodiments, the external subsystem includes a controller. The controller may include a port for interfacing with a computer. A computer may interface with the controller through the port to program patient-specific nerve physiology and stimulation parameters into the controller. The controller may be shaped for placement around a patient's ear. The controller may identify an implant having a unique ID tag, communicate with an implant having the unique ID tag, and send a signal to a transponder located in the implant. In some embodiments, the transponder is a passive RFID transponder. In other embodiments, the transponder is an active transponder. In still further embodiments, the controller provides an RF signal to the implant, senses and records data, and interfaces with a programming device. The controller may also communicate with the implant at preprogrammed intervals. In other embodiments, the controller initiates a stimulation cycle by making a request to the CSS, the request being in the form of an encoded RF waveform including control data. The request may be encrypted.

In some embodiments, the implant provides continuous open loop electrical stimulation to the HGN. In other embodiments, the implant provides closed loop stimulation. The stimulation may be constant, or it may be at preprogrammed conditions. Stimulation may be applied during sleep hours, or it may be applied while the patient is awake. The stimulation may be bi-phasic stimulation of the HGN, with a stimulation pulse width of about 200 microseconds and a stimulation frequency of about 10-40 Hertz. The implant may be hermetically sealed. In other embodiments, the implant delivers multiple modes of stimulation. The stimulation can be in multiple dimensions.

Stimulation may be provided by a neural interface. This stimulation may be applied to the HGN. In certain embodiments, the neural interface includes a plurality of individual electrodes. In further embodiments, the neural interface electrodes include an array of anodes and cathodes, which in some embodiments are a plurality of exposed electrode pairs serving as anode and cathode complementary elements. In certain other embodiments, the electrodes are spot welded to the PCB and include material selected from the group consisting of platinum and iridium. In certain embodiments, the neural interface includes no external wires or leads. In still further embodiments, the neural interface includes a matrix of platinum electrodes coupled to the fascicles of the hypoglossal nerve (HGN). In some embodiments, the neural interface senses neural activity of the nerve it interfaces with, and transmits that sensed neural activity to the core subsystem.

In some embodiments, the core subsystem (CSS) of the implant is included in a silicon chip placed on the top of the printed circuit board PCB, with the chip connected to the neural interface via traced wires printed on the PCB. The chip may be powered by and receive a customized electrode stimulation program protocol from the controller. Upon receiving a request to enter into a stimulation state the CSS selects a trained waveform from memory and starts stimulation by providing an electrical signal to the neural interface. In some embodiments, the core subsystem reports completion of a stimulation state to the controller via an RF communication and optionally goes to an idle state.

Methods for treating obstructive sleep apnea are also disclosed. In one method, a hypoglossal nerve (HGN) is selectively stimulated. A neural interface is implanted in a fascicle of the HGN. The neural interface senses and records neural activity, and feeds the sensed neural activity information into a parameterized control algorithm. In certain embodiments, an external subsystem inductively coupled to an RFID senses and records the neural activity. The algorithm compares the sensed information to a reference data set in real time, transmits in real time an output of the parameterized control algorithm from an external RF interface to an internal RF interface, and from the internal RF interface to a microprocessor. Stimulus information may be calculated and communicated between the external RF interface and the internal RF interface in real time. In another method, bi-phasic electrical stimulation is applied to individual fascicles of the hypoglossal nerve using selectively excitable individual electrodes arranged in a planar field.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention. In the drawings:

FIG. 5 shows an embodiment of an internal subsystem mplant.

FIG. 5A is a breakout view of FIG. 1.

DETAILED DESCRIPTION OF THE PREFERRED EMBODIMENTS

Figure 1:
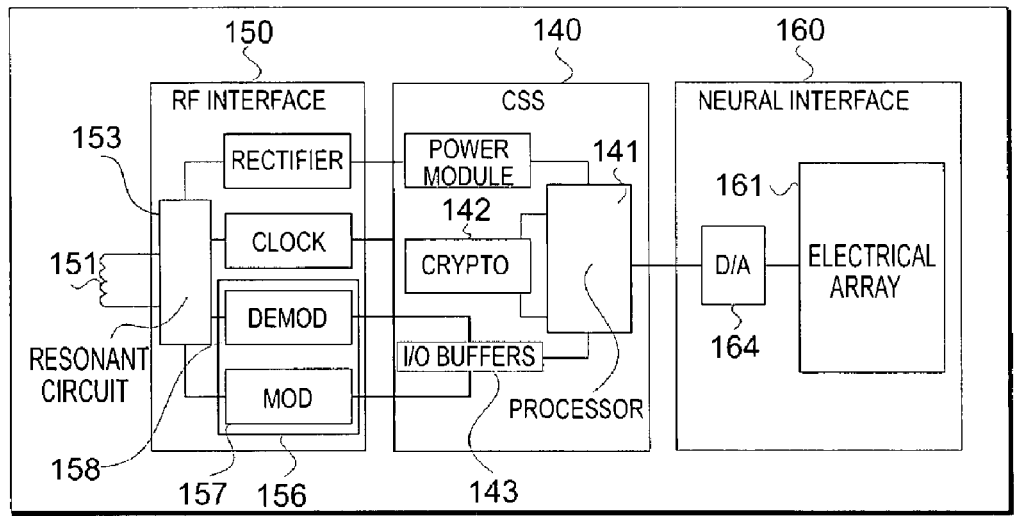
FIG. 1 shows an embodiment of an internal subsystem.

Reference will now be made in detail to the preferred embodiments of the present invention, examples of which are illustrated in the accompanying drawings.

One embodiment the present invention includes an external subsystem and an internal subsystem. In certain embodiments, the external subsystem includes one or more of (1) a controller, (2) an external RF interface, and (3) an optional power source. The internal subsystem may include an implant. In certain embodiments, the implant includes one or more of (1) a neural interface which can include an array of electrodes where at least one electrode contacts a nerve, (2) a core subsystem, and (3) an internal RF interface. In some embodiments, the neural interface may further include a digital to analog signal converter and a multiplexer.

In some embodiments the core subsystem may include a microprocessor. The microprocessor may have a micrologic CPU and memory to store protocols selective to a patient. The microprocessor may be part of an integrated silicon package. In still further embodiments, the internal RF interface may include one or more of a transponder, internal antenna, modulator, demodulator, clock, and rectifier. The transponder can be passive or active. In some embodiments, one or more of a controller, external RF interface, and optional power source are positioned on the skin of a user/patient, typically directly over or in close proximity to, an implant.

In certain embodiments, the external subsystem controller can be in the form of an earpiece or patch including any one or more of the controller, external RF interface, and optional power source, e.g., a battery, AC to DC converter, or other power sources known to those skilled in the art. In certain embodiments, the external subsystem can send and receive control logic and power using an external RF interface. In such embodiments, the external subsystem can further include one or more of a crypto block, data storage, memory, recording unit, microprocessor, and data port. In some embodiments the microprocessor may have a micrologic CPU and memory to store protocols selective to a patient. The microprocessor may be part of an integrated silicon package.

Each of the components of various embodiments of the claimed invention is described hereafter. In certain embodiments, the present invention is an open loop system. In other embodiments the present invention is a closed loop system. The components of the embodiments can be rearranged or combined with other embodiments without departing from the scope of the present invention.

The Internal Subsystem

In certain embodiments, the internal subsystem includes an implant, which includes one or more of (1) a core subsystem, (2) a neural interface, and (3) an internal RF interface. Certain embodiments of the implant components and component arrangements are described below.

Implant Components

The following paragraphs describe embodiments of the implant of the present invention, which includes one or more of a core subsystem, neural interface, and internal RF interface components.

The Core Subsystem

FIG. 1 shows an embodiment of the internal subsystem 100. In certain embodiments the internal subsystem 100 includes an implant 105 (non-limiting representative embodiments of implant 105 are shown in FIGS. 3, 5, 5A, 6A, 6B, and 8) which may have a core subsystem 140. The middle portion of FIG. 1 shows a detailed view of an embodiment of the core subsystem 140. The core subsystem 140 may include one or more of a power module 144, microprocessor 141, crypto block 142, and input output buffer 143. In certain embodiments, the microprocessor 141 may have a micrologic CPU, and may have memory to store protocols selective to a patient. In the embodiment shown, the core subsystem includes a power module 144, a core subsystem microprocessor 141 for managing communication with an external RF interface 203, at least one I/O buffer 143 for storing inbound and outbound signal data, and a core subsystem crypto block 142. In some embodiments, the core subsystem microprocessor 141 communicates with the external RF interface 203 in full duplex. The core subsystem microprocessor 141 may generate signals for controlling stimulation delivered by the neural interface 160, and it may processes signals received from the neural interface 160. In certain embodiments, the core subsystem microprocessor logic includes an anti-collision protocol for managing in-range multiple transponders and readers, a management protocol for reset, initialization, and tuning of the implant 105, and a protocol to facilitate the exchange of data with the neural interface 160. The core subsystem microprocessor 141 is programmable and may further include an attached non-volatile memory. The microprocessor 141 may be a single chip 145 or part of an integrated silicon package 170.

Figure 2:
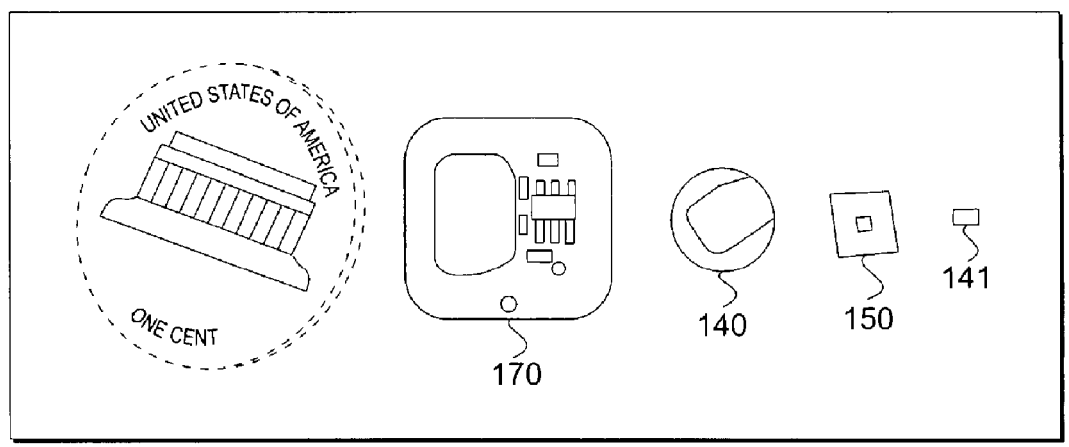
FIG. 2 shows an embodiment of an internal subsystem with the core subsystem and internal RF interface in a silicon package.

FIG. 2 shows an embodiment of an internal subsystem 100 with the core subsystem 140 and internal RF interface 150 in a silicon package 170. For size comparison, FIG. 2 shows the core subsystem 140, internal RF interface 150, and core subsystem microprocessor 141 next to the silicon package 170.

The Neural Interface

The right portion of FIG. 1 shows an embodiment of a neural interface 160. The neural interface 160 can include an array of electrodes 161 where at least one electrode 161 contacts a nerve. In one embodiment, the neural interface 160 includes an array of 10 to 16 electrodes 161. This arrangement is exemplary only however, and not limited to the quantity or arrangement shown. The core subsystem 140 connects to the neural interface 160, and controls neural interface stimulation. In the embodiment shown, the neural interface 160 is attached to the printed circuit board 130. In some embodiments, the neural interface 160 may further include a digital to analog signal converter 164 and a multiplexer 166. In certain embodiments the multiplexer 166 is included on the printed circuit board 130. In other embodiments, the multiplexer 166 is included on a thin layer film or flexible membrane around the surface of the chip.

In the embodiment shown, the neural interface 160 receives power from RF waves received by the implant 105. In one embodiment, the D/A converter 164 uses the RF waves to power one or more capacitors 165, which may be located in the converter 164. In certain embodiments, the capacitors 165 are arranged in an array on a microfilm. These capacitors 165 store charges, which are used to generate analog burst pulses for delivery by the neural interface 160. In embodiments including a multiplexer 166, the multiplexer 166 may be used to deliver power to multiple capacitors 165, and can be used to deliver power to multiple electrodes 161 in the neural interface 160. In still further embodiments, the multiplexer 166 is programmable.

In certain embodiments, the neural interface 160 is physically located on the opposite side of the printed circuit board 130 to which the core subsystem 140 is attached. In other embodiments, the one or more electrodes 161 are physically separated from the core subsystem 140 by the printed circuit board 130. Each electrode 161 connects to the core subsystem 140 through wires 133 (e.g., traced wires) on the printed circuit board 130. This layered approach to separating the core subsystem 140 from the electrodes 161 has significant benefits in the bio-compatible coating and manufacturing of the implant. By minimizing the area exposed to the HGN, the bio-compatible coating is only required in the area surrounding the exposed parts of the electrodes 161.

The electrodes 161 may be manufactured with biocompatible material coating. In certain embodiments, the electrodes may include embedded platinum contacts spot-welded to a printed circuit board 130 on the implant 105. The electrodes 161 may be arrayed in a matrix, with the bottoms of the electrodes 161 exposed for contact to the HGN. Since the electrodes 161 attach to the top portion of the core subsystem 140 through leads on the printed circuit board, there is no need for wire-based leads attached to the contact points, allowing for miniaturization of the electrodes 161.

Figure 3:
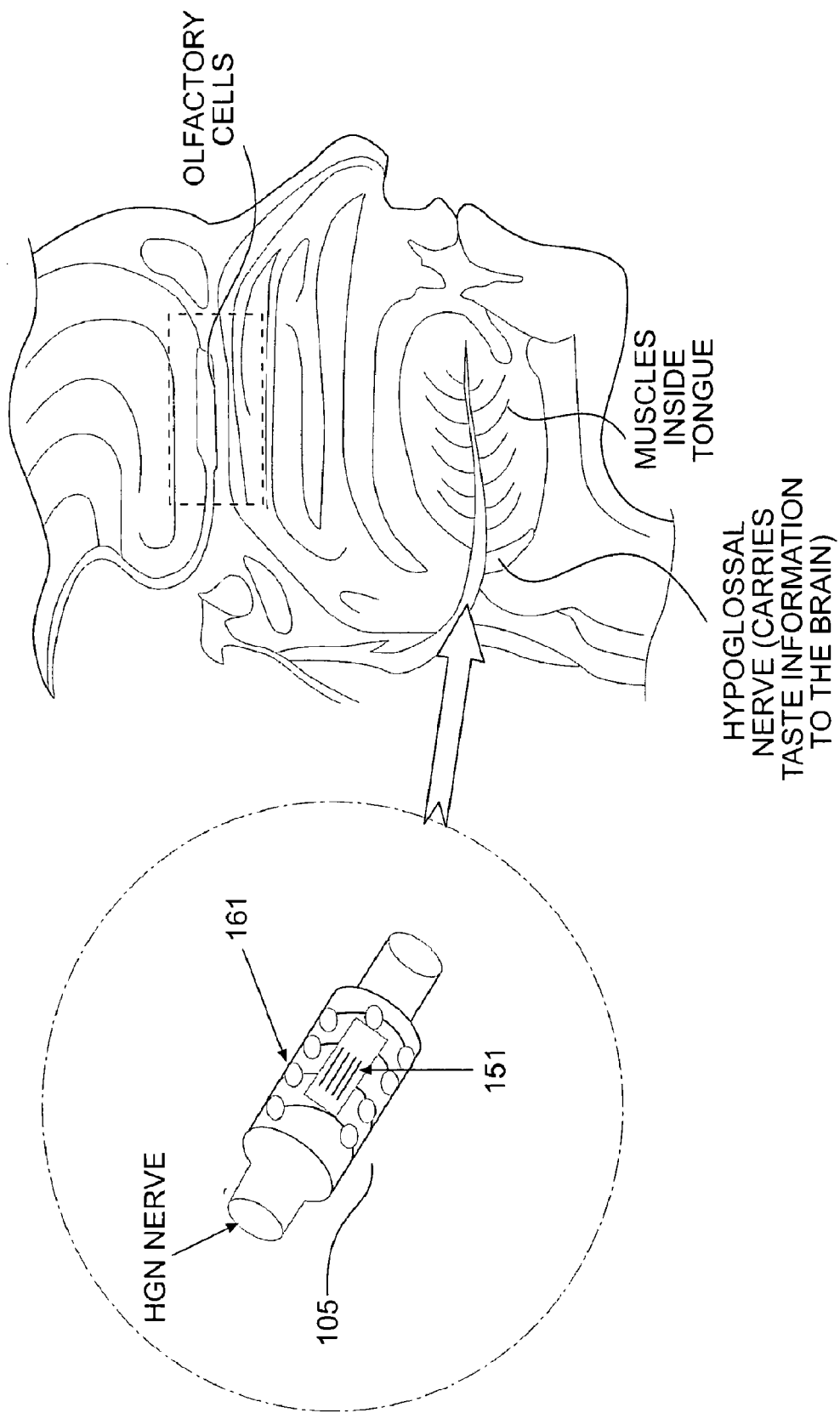
FIG. 3 shows a hypoglossal nerve an implant.

FIG. 3 shows a hypoglossal nerve implanted with a neural interface 160. In one embodiment, exposed portions of the neural interface 160 deliver selective stimulation to fascicles of the HGN. Selective stimulation allows co-activation of both the lateral HGN branches, which innervate the hypoglossus (HG) and styloglossus (SG), and the medial branch. This selective stimulation of HG (tongue retraction and depression) and the SG (retraction and elevation of lateral aspect of tongue) results in an increased maximum rate of airflow and mechanical stability of the upper airway (UAW). Selective stimulation is a unique approach to nerve stimulation when implanted on the hypoglossal nerve (HGN). The neural interface 160 may also sense the neural activity of the nerve it interfaces with and may transmit that sensed activity to the core subsystem microprocessor 141.

Figure 4:
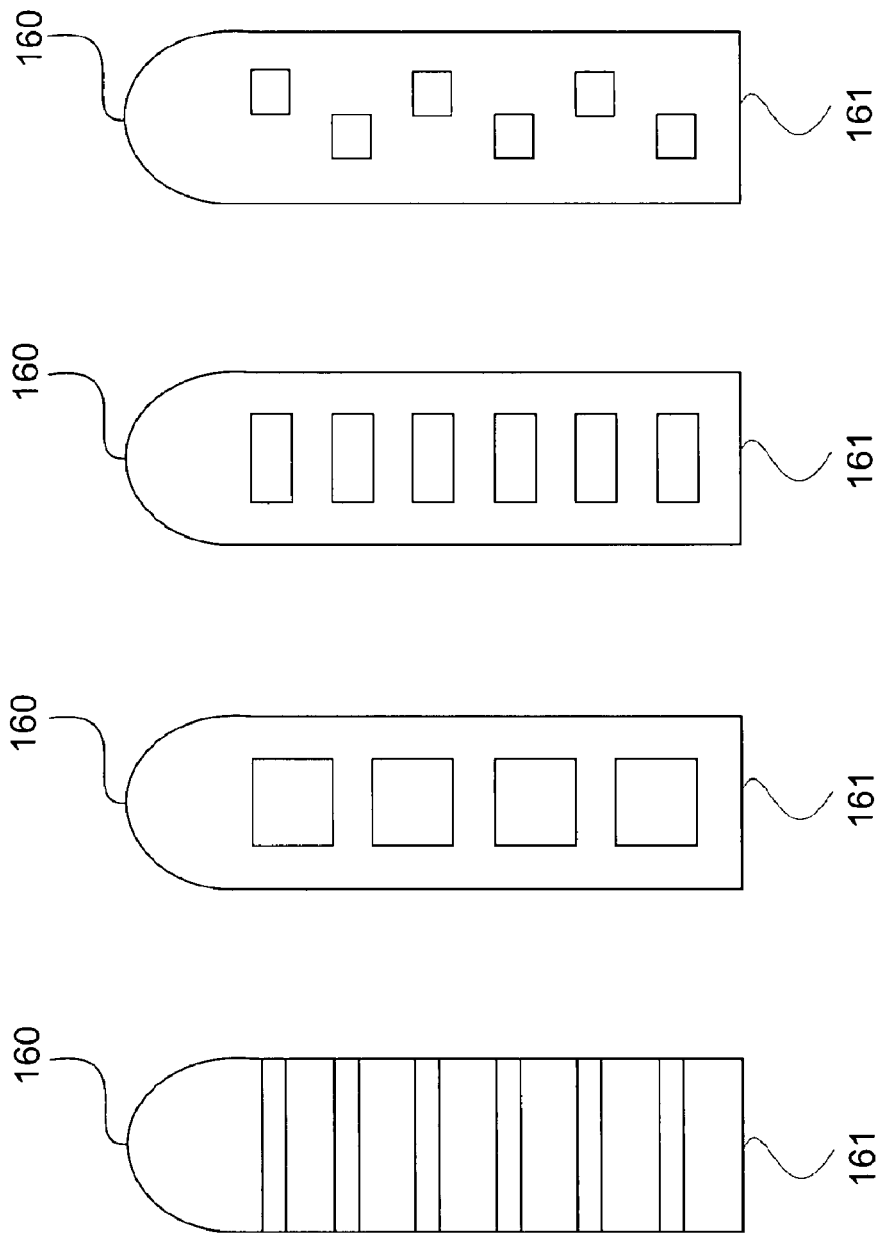
FIG. 4 shows multiple embodiments of neural interface electrode arrays.

FIG. 4 shows embodiments of neural interface electrode arrays. These embodiments are exemplary only, and the arrays are not limited to the quantity or arrangement of the electrodes shown in the figure. In one embodiment, at least one electrode 161 is in contact with a nerve. In certain embodiments, the electrodes 161 may be in the shape of a linear, regular, or irregular array. In certain embodiments, the electrode 161 array may be in a form suitable for wrapping around a nerve (e.g., a helical shape or spring-like shape as shown in FIG. 3). The electrodes 161 may also be arranged in a planar form to help reshape the nerve and move the axons closer to the electrodes 161. This facilitates access to multiple nerve axons, which enables multiple modes of stimulation for enhanced UAW dilation and stability. With a planar form factor, stimulation can also be delivered in two dimensions, enabling optimal excitation of the functional branches of the nerve. Excitation happens through bi-phasic electrical stimulation of individual electrodes 161.

The Internal RF Interface

The left portion of FIG. 1 shows a detailed view of an embodiment of the internal RF interface 150. The internal RF interface 150 may include one or more of a transponder 156, internal antenna 151, modulator 157, demodulator 158, clock 159, and rectifier. The transponder 156 can be passive or active. In certain embodiments, the internal RF interface 150 can send and/or receive one or more of (1) control logic, and (2) power. In still further embodiments, the internal RF interface 150 delivers one or more of power, clock, and data to the implant core subsystem 140. In certain embodiments the data is delivered via a full duplex data connection. In some embodiments, the internal RF interface 150 sends data (e.g., function status) of one or more electrodes 161 to a controller 205, described below, for review by a technician or physician.

The internal RF interface 150 operates according to the principle of inductive coupling. In an embodiment, the present invention exploits the near-field characteristics of short wave carrier frequencies of approximately 13.56 MHz. This carrier frequency is further divided into at least one sub-carrier frequency. In certain embodiments, the present invention can use between 10 and 15 MHz. The internal RF interface 150 uses a sub carrier for communication with an external RF interface 203, which may be located in the controller 205. The sub-carrier frequency is obtained by the binary division of the external RF interface 203 carrier frequency. In the embodiment shown, the internal RF interface 150 is realized as part of a single silicon package 170. The package 170 may further include a chip 145 which is a programmable receive/transmit RF chip.

In certain embodiments, the internal RF interface 150 also includes a passive RFID transponder 156 with a demodulator 158 and a modulator 157. The transponder 156 uses the sub carrier to modulate a signal back to the external RF interface 203. In certain embodiments, the transponder 156 may further have two channels, Channel A and Channel B. Channel A is for power delivery and Channel B is for data and control. The transponder 156 may employ a secure full-duplex data protocol.

The internal RF interface 150 further includes an inductive coupler 152, an RF to DC converter 155, and an internal antenna 151. In certain embodiments, the internal antenna 151 includes a magnetic component. In such embodiments, silicon traces may be used as magnetic antennas. In other embodiments, the antenna may be a high Q coil electroplated onto a silicon substrate. A parallel resonant circuit 153 may be attached to the internal antenna 151 to improve the efficiency of the inductive coupling. The internal antenna 151 may be realized as a set of PCB traces 133 on the implant 105. Size of the antenna traces is chosen on the basis of power requirements, operating frequency, and distance to the controller 205. Both the internal RF interface 150 and the core subsystem microprocessor 141 are powered from an RF signal received by the internal antenna 151. A shunt regulator 154 in the resonant circuit 153 keeps the derived voltage at a proper level.

Implant Component Arrangement

The implant 105 may be located on any suitable substrate and may be a single layer or multi-layer form. FIG. 5 shows an implant 105 constructed as a single integrated unit, with a top layer 110 and a bottom layer 110 which may be implanted in proximity to, in contact with, or circumferentially around a nerve, e.g., the hypoglossal nerve. FIG. 5A is a breakout view of FIG. 5.

In certain embodiments, implant components are layered on a nerve. This alleviates the need for complex wiring and leads. In FIGS. 5 and 5A, the top layer 110 includes a core subsystem 140, an internal RF interface 150, and a neural interface 160. The top layer 110 serves as the attachment mechanism, with the implant components on the bottom layer 110. The neural interface 160 may be surface bonded to contacts on a printed circuit board 130. The bottom layer 110 is complementary to the top layer 110, and serves as an attachment mechanism so that the implant 105 encompasses the HGN. Although conductive parts in contact with the HGN may be located at any suitable position on the implant 105, in the embodiment shown in FIGS. 5 and 5A, the bottom layer 110 has no conductive parts.

In the embodiment shown in FIGS. 5 and 5A, and as described above, the core subsystem 140 is included in a silicon package 170 (FIG. 2) attached to a printed circuit board (PCB) 130 on the top layer 110. The PCB 130 has a first side 131 and a second side 132. The silicon package 170 is placed on a first side 131 of the printed circuit board 130. In certain embodiments the PCB 130 may be replaced with a flexible membrane substrate. In the embodiment shown, the silicon package 170 further includes the internal RF interface 150. The neural interface 160 attaches to the second side 132 of the PCB 130. In this embodiment, the neural interface 160 (FIG. 6B) further includes a plurality of neural interface electrodes 161 (FIG. 4) arranged into anode and cathode pairs 162/163, shown in this embodiment as an array of 10 to 16 elements. The number and arrangement of anode and cathode pairs 162/163 is exemplary only, and not limited to the embodiment shown. The silicon package 170 (FIG. 2) connects to the anode and cathode pairs 162/163 via traced wires 133 printed on the PCB 130.

Figure 6A:
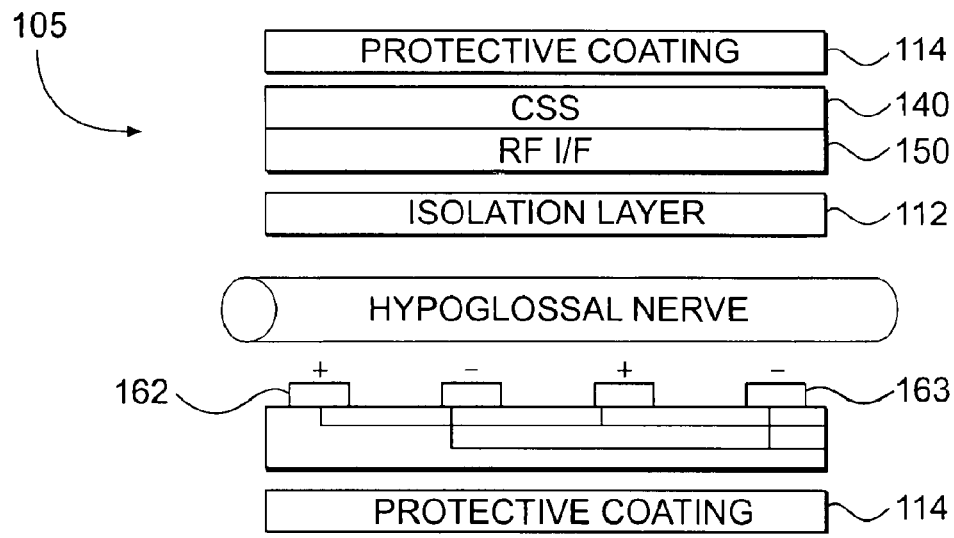
FIG. 6A shows an embodiment of an internal subsystem with the neural interface electrodes on the bottom layer of the implant.
Figure 6B:
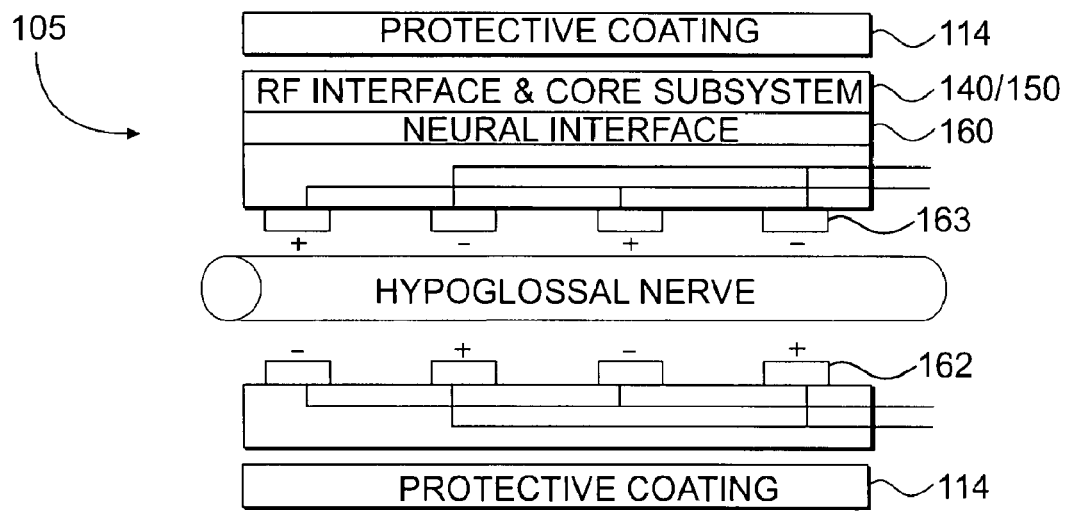
FIG. 6B shows an embodiment of an internal subsystem with the neural interface electrodes on the top and bottom layers of the implant.

In other embodiments, such as the one shown in FIG. 6A, the neural interface electrode anode and cathode pairs 162/163 are located on the bottom layer 110 of the implant 105. In still other embodiments, such as the one shown in FIG. 6B, the neural interface electrode anode and cathode pairs 162/163 are located on both the top and the bottom layers 110/120. The matrix arrangement of electrodes 161 provides multiple nerve stimulating points, and has several advantages. The matrix arrangement allows a web of nerve fascicles of the hypoglossal nerve to be accessed, enabling selective stimulation of particular areas of the nerve. In some embodiments, power is delivered to the matrix of electrodes 161 from the D/A converter 164 to capacitors 165 via a multiplexer 166.

The implant 105 may further include an isolation layer 112 (FIG. 6A). In certain embodiments a protective coating 114 (FIGS. 6A and 6B) may be applied to the top and bottom layers 110/120 of the implant 105. The implant 105 may further be coated with a protective coating 114 for biological implantation. Further, in certain embodiments all or a portion of the device may be encased in a biocompatible casing. In such embodiments, the casing may be a material selected from the group consisting of one or more titanium alloys, ceramic, and polyetheretherketone (PEEK).

The External Subsystem

Figure 7:
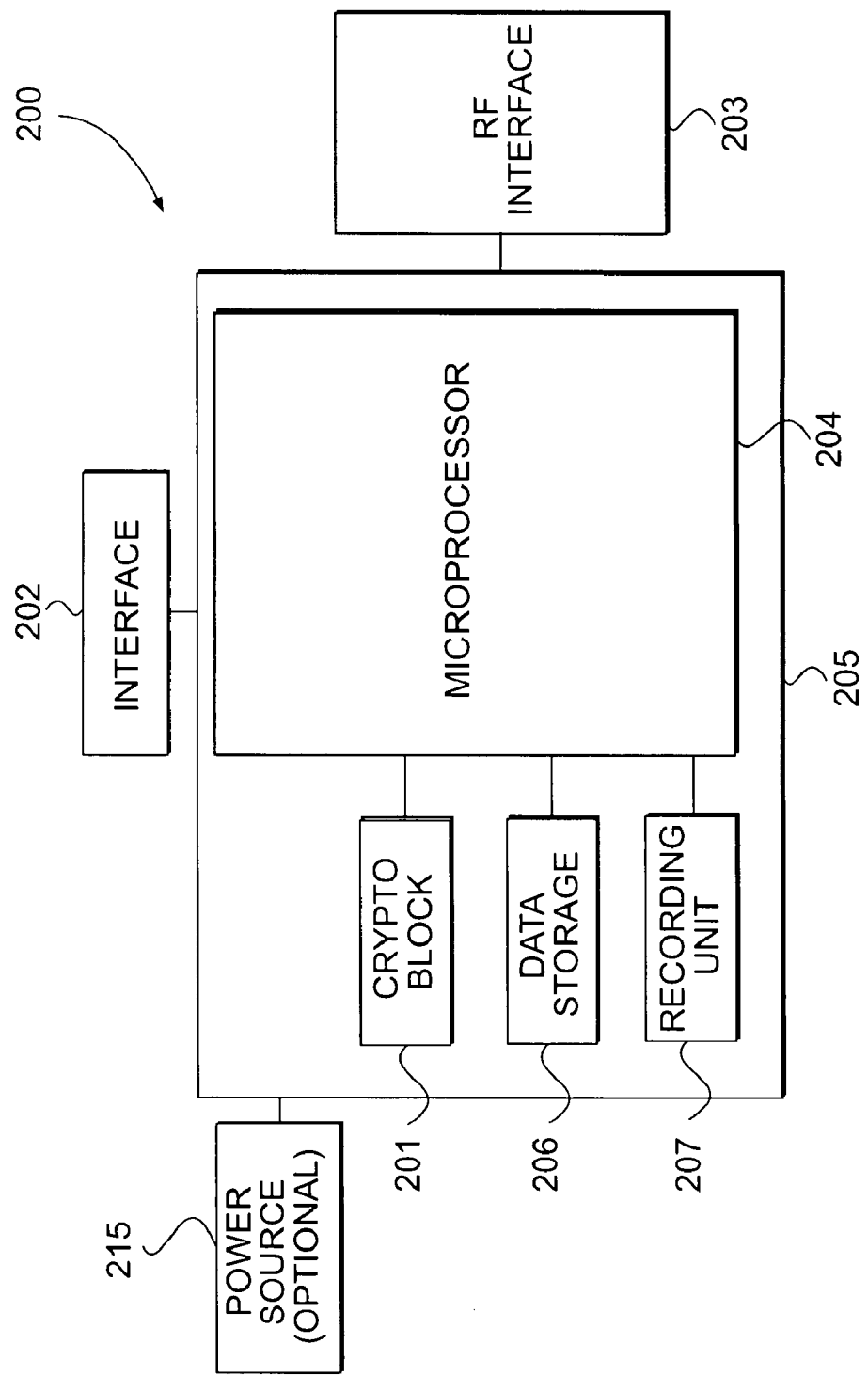
FIG. 7 shows an embodiment of an external subsystem with a controller.

In certain embodiments, the external subsystem 200 may include one or more of (1) a controller, (2) an external RF interface and (3) an optional power source. An embodiment of an external subsystem 200 including these elements is shown in FIG. 7. Typically the external subsystem 200 is located externally on or near the skin of a patient.

The Controller

FIG. 7 shows an embodiment of an external subsystem 200 with a controller 205. The controller 205 controls and initiates implant functions. In other embodiments, the controller 205 may be part of the internal subsystem 100 instead of external subsystem 200, and in still further embodiments, portions of the controller 205 may be in both the external and internal subsystems 200/100. In certain embodiments, the controller 205 may further have one or more of a controller crypto block 201, data storage 206, a recording unit 207, and a controller microprocessor 204. In some embodiments the controller microprocessor 204 may have a micrologic CPU and memory to store protocols selective to a patient. The controller microprocessor 204 is programmable and may further include an attached non-volatile memory. The microprocessor 204 may be a single chip or part of an integrated silicon package.

In certain embodiments, the controller may further include includes one or more of an external RF interface having RF transmit and receive logic, a data storage that may be used to store patient protocols, an interface (e.g., a USB port), a microprocessor, an external antenna, a functionality to permit the controller to interface with a particular implant, and an optional power source. In certain embodiments, the controller electronics can be either physically or electromagnetically coupled to an antenna. The distance between the external RF interface antenna (not shown) and the implant 105 may vary with indication. In certain embodiments, distance is minimized to reduce the possibility of interference from other RF waves or frequencies. Minimizing the distance between the external antenna and the implant 105 provides a better RF coupling between the external and internal subsystems 200/100, further reducing the possibility of implant activation by a foreign RF source. An encrypted link between the external and internal subsystems 200/100 further reduces the possibility of implant activation by foreign RF. In other embodiments, one or more of the internal antenna 151 and external antennas 209 are maintained in a fixed position. Potential design complexity associated with internal RF interface antenna 151 orientation is minimized through the ability to position the external RF interface antenna in a specific location (e.g., near the patient's ear). Even if the patient moves, the internal RF interface antenna 151 and controller 205 remain coupled.

In certain other embodiments, the controller 205 can also serve as (1) a data gathering and/or (2) programming interface to the implant 105. The controller 205 has full control over the operation of the implant 105. It can turn the implant 105 on/off, and may be paired to the implant 105 via a device specific ID, as described herein below with respect to use of the implant 105 and controller 205 of the present invention. In still further embodiments, the controller microprocessor 204 calculates stimulus information. The stimulus information is then communicated to the implant 105. The implant 105 then provides a calculated stimulus to a nerve. In another embodiment, the controller 205 preloads the implant 105 with an algorithmic protocol for neural stimulation and then provides power to the implant 105.

External RF Interface

In the embodiment shown in FIG. 7, the external subsystem 200 includes an external RF interface 203 that provides an RF signal for powering and controlling the implant 105. The external RF interface 203 can be realized as a single chip, a plurality of chips, a printed circuit board, or even a plurality of printed circuit boards. In other embodiments, the printed circuit board can be replaced with a flexible membrane. The external RF interface 203 may include one or more of a transponder 208 (not shown), external antenna (not shown), modulator 210 (not shown), and demodulator 211 (not shown), clock 212 (not shown), and rectifier 213 (not shown) (not shown). The external RF interface transponder 208 can be passive or active. In certain embodiments, the external RF interface 203 can send and/or receive one or more of (1) control logic, and (2) power. In still further embodiments, the external RF interface 203 delivers one or more of power, clock, and data to one or more of the external subsystem controller 205 and the internal subsystem 100 via the internal RF interface 150. In certain embodiments the data is delivered via a full duplex data connection.

In an embodiment, the external RF interface 203 operates at a carrier frequency of approximately 13.56 MHz. In certain embodiments, the external RF interface 203 can operate between 10 and 15 MHz. This carrier frequency is further divided into at least one sub-carrier frequency. The sub-carrier frequency is obtained by binary division of the external RF interface 203 carrier frequency. The external RF interface 203 uses the sub carrier for communication with the internal RF interface 150. The external RF interface transponder 208 (not shown) uses the sub carrier to modulate a signal to the internal RF interface 150. The transponder 208 (not shown) may further have two channels, Channel A and Channel B. Channel A is for power delivery and Channel B is for data and control. The transponder 208 (not shown) may employ a secure full-duplex data protocol.

In certain embodiments, the external RF interface 203 may further include a demodulator 211 (not shown) and a modulator 210 (not shown). In still further embodiments, the external RF interface 203 further includes an external antenna. In certain embodiments, the external antenna includes a magnetic component. In such embodiments, silicon traces may be used as magnetic antennas. The antenna may be realized as a set of PCB traces. Size of the antenna traces is chosen on the basis of power requirements, operating frequency, and distance to the internal subsystem 100. In certain embodiments, the external antenna may transmit the power received by internal subsystem 100. In certain other embodiments, the external antenna may be larger, and have a higher power handling capacity than the internal antenna 151, and can be realized using other antenna embodiments known by those skilled in the art.

In certain embodiments, the external subsystem 200 is loosely coupled to an optional power source 215. In one embodiment, the controller power source 215 is not co-located with the external RF interface antenna. The external power source 215 may be in one location, and the external RF interface 203 and optionally the controller 205 are in a second location and/or third location. For example, each of the power source 215, controller 205 and external RF interface 203 can be located in difference areas. In one embodiment, the power source 215 and the controller 205 and the external RF interface 203 are each connected by one or more conductive members, e.g. a flexible cable or wire. Additionally, in certain embodiments, the controller 205 and optional power source 215 may be co-located, and the external RF interface 203 may be located elsewhere (i.e., loosely coupled to the controller 205). In such embodiments, the external RF interface 203 is connected to the controller 205 by a flexible cable or wire.

Since the power source 215 may be separately located from the controller 205 and/or external RF interface antenna, a larger power source 215 can be externally located but positioned away from the nerve that requires stimulation. Further, to reduce wasted power, a larger external RF interface antenna can be used. This provides the advantage of less discomfort to a user and therefore enhances patient compliance.

Such embodiments can also provide power to 2, 3, 4, 5 or more loosely coupled external RF interfaces 203. Thus, each external RF interface 203 can be positioned at or near the site of an implant 105 without the need for a co-located power source 215. In certain embodiments, each external RF interface 203 draws power from a single power source 215, and thus a single power source 215 powers a plurality of implants 105. Of course, the amount of power provided to each implant 105 will vary by indication and distance between the external RF interface 203 and the implant 105. The greater the distance between the external RF interface 203 and the implant 105, the greater the power level required. For example, a lower power is generally required to stimulate peripheral nerves, which are closer to the surface of the skin. As apparent to one of skill in the art, the power received at the implant 105 must be high enough to produce the desired nerve stimulus, but low enough to avoid damaging the nerve or surrounding tissue.

The external RF interface 203 may further include a programmable receive/transmit RF chip, and may interface with the controller crypto unit 201 for secure and one-to-one communication with its associated implant 105. The external RF interface 203 includes a parameterized control algorithm, wherein the parameterized control algorithm compares the sensed information to a reference data set in real time. The algorithm may be included in the controller microprocessor 204. Depending upon the patient's size and severity of disease state, the algorithm will vary a number of parameters which include frequency, amplitude of the signal, number of electrodes involved, etc.

Interaction With Outside Information Sources

The external subsystem controller 205 may also interface with a computer. In some embodiments, the controller interface 202 is a built-in data port (e.g., a USB port). Via the controller interface 202 a computer may tune (and re-tune) the implant system, and transfer historical data recorded by the implant 105. The controller 205 may obtain and update its software from the computer, and may upload and download neural interface data to and from the computer. The software may be included in the controller microprocessor 204 and associated memory. The software allows a user to interface with the controller 205, and stores the patient's protocol program.

External Subsystem Design

Figure 8:
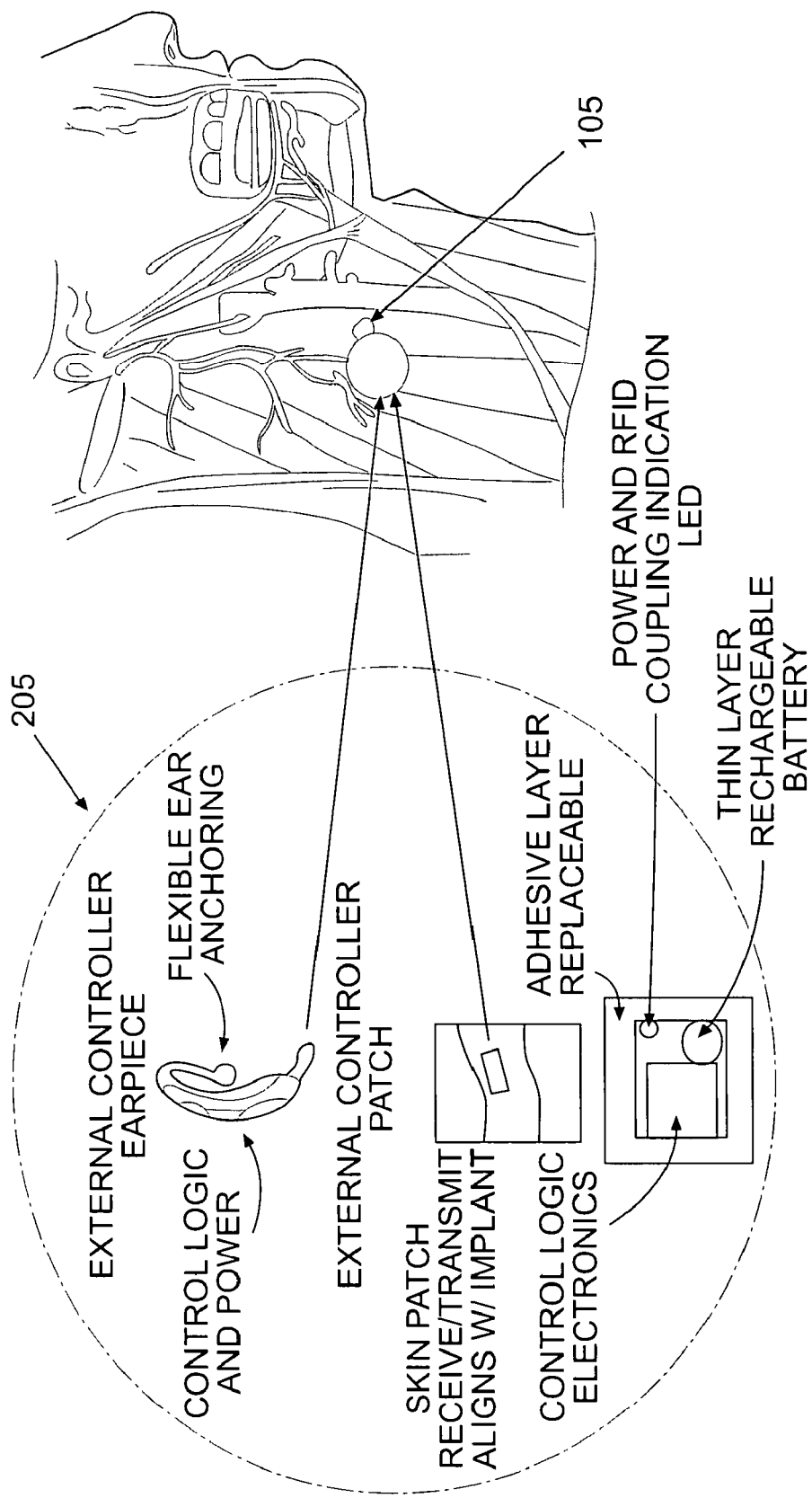
FIG. 8 shows two embodiments of the external controller.

The external subsystem 200 can be of regular or irregular shape. FIG. 8 shows two embodiments of an external subsystem controller 205, one with the controller 205 included with an earpiece much like a Bluetooth earpiece, and one with the controller 205 included with a patch. In the embodiments shown, potential design complexity associated with internal RF antenna 151 orientation is minimized through the single and fixed position of the controller 205. The patient may move and turn without disrupting the coupling between the controller 205 and the internal antenna 151. In the embodiment with the controller 205 in an earpiece, a flexible receive/transmit tip in the earpiece aligns the controller external RF interface antenna with the implant 105. In the embodiment with the controller 205 in a patch, the patch is aligned with the implant 105 and placed skin. The patch may include one or more of the controller 205, a replaceable adhesive layer, power and RFID coupling indication LED, and a thin layer rechargeable battery. Still further embodiments include incorporation of the external subsystem 200 into a watch-like device for, e.g., the treatment of arthritic pain, or in a belt. Yet another range of variations are flexible antennas and the controller RF chip woven into clothing or an elastic cuff, attached to controller electronics and remotely powered. Controller 205 designs may be indication specific, and can vary widely.

The controller 205 embodiments in FIG. 8 are exemplary only, and not limited to those shown.

Communication with the Implant as a Function of Design

The distance between this contact area and the actual implant 100 on a nerve is 1 to 10 cm, typically 3 cm, through human flesh. This distance, along with the controller crypto unit 201 and the core subsystem crypto unit 142 in the implant 100, reduces potential interference from other RF signals.

Implant and Controller Positioning

Prior to implantation of the present invention for the treatment of sleep apnea, patients are diagnosed in a sleep lab, and an implant 105 is prescribed for their specifically diagnosed condition. Once diagnosis is complete, the implant 105 is surgically implanted in the patient's body, typically on or in the vicinity of a nerve. In certain embodiments, the implant 105 is implanted on the HGN. In such embodiments, the implant 105 may be implanted below the ear unilaterally at the sub-mandibular triangle, encasing the hypoglossal nerve.

Stimulation of the HGN can act to maintain nerve activity. Hence in certain embodiments, the present invention can maintain muscular tone (e.g., in the tongue, thereby preventing apnea). Therefore, in certain embodiments, controller 205, described in more detail above, activates implant 105 to stimulate HGN activity to ameliorate the negative physiological impact associated with insufficient tone muscles caused by, e.g., insufficient HGN activity.

Once implanted, the implant 105 is used to stimulate the nerve. In embodiments where the device is implanted in a manner to stimulate the HGN, the implant 105 delivers tone to the tongue. Maintaining tongue muscle tone stops the tongue from falling back and obstructing the upper airway. The stimulation may be provided continuously during sleep hours, or upon preprogrammed patient-specific intervals. The implant 105 may also sense and record neural activity.

Implant and Controller Security

In certain embodiments, the controller 205 identifies the patient's unique ID tag, communicates with and sends signals to the implant 105. In certain embodiments, a controller crypto unit 201 may be installed to ensure that communication between the controller 205 and the implant 105 is secure and one-to-one. The controller crypto unit 201 may include the implant's unique ID tag.

In particular, the implant 105 may have a unique ID tag, which the controller 205 can be programmed to recognize. A controller microprocessor 204 confirms the identity of the implant 105 associated with the controller 205, thereby allowing setting of the patient's specific protocol. The setting may be accomplished using a computer interfaced with the controller 205 through an interface 202 on the controller 205.

More particularly, once the controller crypto unit 201 establishes a link with the core subsystem crypto unit 142, the controller 205 communicates a stimulation scenario to the core subsystem microprocessor 141. The controller 205 initiates a stimulation cycle by making a request to the core subsystem 140 by sending an encoded RF waveform including control data via the external RF interface 203. The core subsystem 140 selects a trained waveform from memory and transmits the stimulation waveform to the core subsystem microprocessor 141. Once the core subsystem microprocessor 141 receives the waveform, the core subsystem 140 generates a stimulating signal for distribution to the neural interface 160.

Interaction with the Implant In certain embodiments, the controller 205 prevents self-activation or autonomous operation by the implant 105 by handshaking. Handshaking occurs during each communications cycle and ensures that security is maintained. This prevents other devices operating in the same frequency range from compromising operation of the implant 105. Implant stimulus will not commence unless an encrypted connection is established between the external RF interface 203 and the implant 105. This serves as an anti-tampering mechanism by providing the implant 105 with a unique ID tag. The external controller 205 is matched, either at the point manufacture or by a physician, to a particular ID tag of the implant 105, typically located in an EPROM of the implant 105. In certain embodiments, the EPROM may be included in the core subsystem microprocessor 141. In other embodiments, the EPROM may be included in the controller microprocessor 204. This prevents alien RF interference from 'triggering' activation of the implant 105. While arbitrary RF sources may provide power to the implant 105, the uniquely matched controller 205 establishes an encrypted connection before directing the implant 105 to commence stimulus, thereby serving as a security mechanism.

System Programming

Desired system programming is determined by measuring a patient's tongue activity against predetermined stimulation protocols. The effectiveness of the neural interface 160 stimulation protocols are measured until a desired tongue stimulation level is achieved. Once a desired tongue stimulation level is achieved, those protocols are programmed into the controller 205. Stimulation may be programmed for delivery in an open loop or closed loop at a suitable frequency. In certain embodiments, a stimulation frequency of about 10-40 Hz is used. Stimulation may also be delivered in pulses, with pulse widths about 100 to 300 microseconds, more typically 200 microseconds. Although any suitable pulse width can be used, preferred pulses are at a width that simultaneously prevent nerve damage and reduce or eliminate corrosion of neural interface electrodes. After the controller 205 is programmed, the patient activates the controller 205 at bed time or at desired intervals.

In certain embodiments, controller 205 can also determine when the patient is asleep, and stimulate the HGN based on that determination. In order to determine when the patient is asleep, controller 205 can include one or more sensors that generate signals as a function of the activity and/or posture of the patient. In such embodiments, controller 205 determines when the patient is asleep based on the signal. Controller 205 can also have an acoustic sensor, to indicate when snoring starts, and can determine whether the patient is asleep based on the presence of snoring. In other embodiments the patient may enter an input into the controller 205 telling it to commence treatment. However, as noted above, controller 205 can be activated by a user and then function in a manner such that the implant is continuously active until the patient awakens and manually deactivates the controller by pressing a button on the controller 205 or by moving the controller 205 out of range of the implant.

This electrical stimulation provides a signal to the HGN and starts the treatment of the airway obstruction. Upon completion of one cycle, the duration of which is determined in the tuning phase of the implantation procedure, described above, the core subsystem 140 can report completion back to the controller 205 via RF communication, and optionally goes to an idle state until receiving another set of instructions.

As described above, in certain embodiments, the implant 105 is externally powered by near field RF waves, the RF waves are inductively converted to DC power, which powers the implant 105 and delivers electrical signals to selected elements of the neural interface 160. The implant uses between 0.1 to about 1 milliamps, preferably averaging about 0.5 milliamps of current and about 10 to 30 microwatts of power.

In some embodiments, the near field RF waves are emitted from the controller 205. In certain embodiments, controller 205 can be powered by an optional power source 215, e.g., a battery, AC to DC converter, or other power source known to those skilled in the art.

Other embodiments of the apparatus and methods described can be used in the present invention. Various alternatives, substitutions and modifications for each of the embodiments and methods of the invention may be made without departing from the scope thereof, which is defined by the following claims. All references, patents and patent applications cited in this application are herein incorporated by reference in their entirety.

What is claimed is:

1. An implantable neurostimulator system for treating obstructive sleep apnea, comprising:
   an implant having a top and a bottom layer, the bottom layer serving as an attachment mechanism such that the bottom layer of the implant is adapted to be coupled to and at least partially surround a Hypoglossal nerve (HGN) and attaches to the top layer of the implant;
   a printed circuit board (PCB) attached to the top layer of the implant, the PCB having a first and a second opposing sides;
   a neural interface attached to the PCB;
   a core subsystem (CSS) attached to the first side of the PCB and electrically connected to the neural interface;
   a radio frequency (RF) interface attached to the PCB and electrically connected to the CSS; and
   an external programmable controller configured to power and control the implant,
   wherein the core subsystem is configured to select a trained waveform from memory and start stimulation by providing an electrical signal to the neural interface upon receiving a request to enter into a stimulation state, and
   wherein the core subsystem is configured to report completion of a stimulation state to the controller via an RF communication and go to an idle state.

2. The system of claim 1, further comprising a plurality of individual electrodes.

3. The system of claim 1, wherein the implant is configured to provide stimulation to the HGN at preprogrammed conditions.

4. The system of claim 1, wherein the core subsystem being included in a silicon chip attached to the PCB with the chip connected to the neural interface via traced wires printed on the PCB.

5. The system of claim 1, wherein the silicon chip is configured to be powered by and receive a customized electrode stimulation program protocol from the controller.

6. The system of claim 1, further comprising a matrix of electrodes coupled to one or more fascicles or regions of the HGN.

7. The system of claim 1, wherein the supplied power includes RF energy emitted by the controller.

8. The system of claim 1, wherein the controller is configured to stimulate patient specific nerve physiology and stimulation parameters.

9. The system of claim 1, wherein the controller is shaped for placement around a patient's ear.

10. The system of claim 1, wherein the controller is configured to:
    identify an implant having a unique ID tag;
    communicate with the implant having the unique ID tag; and
    send a signal to a transponder located in the implant.

11. The system of claim 1, wherein the controller is configured to:
provide an RF signal to the implant;
sense and record data; and
interface with a programming device.

12. The system of claim 1, wherein the controller is configured to communicate with the implant at preprogrammed intervals.

13. The system of claim 1, wherein the implant is configured to provide continuous open loop electrical stimulation to the HGN during sleep hours.

14. The system of claim 1, wherein the implant is configured to deliver multiple modes of stimulation.

15. The system of claim 1, wherein the implant is configured to provide stimulation in multiple dimensions.

16. Previously Presented) The system of claim 1, wherein the neural interface does not include external wires or leads.

17. The system of claim 1, wherein the neural interface is configured to stimulate the HGN.

18. The system of claim 1, wherein the neural interface is configured to sense neural activity of the nerve it interfaces with and transmit that sensed neural activity to the core subsystem.

19. An implantable neurostimulator system for treating obstructive sleep apnea, comprising:
an implant having a top and a bottom layer, the bottom layer serving as an attachment mechanism such that the bottom layer of the implant is adapted to be coupled to and at least partially surround a Hypoglossal nerve (HGN) and attaches to the top layer of the implant;
a printed circuit board (PCB) attached to the top layer of the implant, the PCB having a first and a second opposing sides;
a neural interface attached to the PCB;
a core subsystem (CSS) attached to the first side of the PCB and electrically connected to the neural interface;
a radio frequency (RF) interface attached to the PCB and electrically connected to the CSS; and
an external programmable controller configured to power and control the implant,
wherein the core subsystem being included in a silicon chip attached to the PCB with the chip connected to the neural interface via traced wires printed on the PCB.

20. The system of claim 19, further comprising a plurality of individual electrodes.

21. The system of claim 19, wherein the implant is configured to provide stimulation to the HGN at preprogrammed conditions.

22. The system of claim 19, wherein the silicon chip is configured to be powered by and receive a customized electrode stimulation program protocol from the controller.

23. The system of claim 19, further comprising a matrix of electrodes coupled to one or more fascicles or regions of the HGN.

24. The system of claim 19, wherein the core subsystem is configured to select a trained waveform from memory and start stimulation by providing an electrical signal to the neural interface upon receiving a request to enter into a stimulation state.

25. The system of claim 19, wherein the supplied power includes RF energy emitted by the controller.

26. The system of claim 19, wherein the controller is configured to stimulate patient specific nerve physiology and stimulation parameters.

27. The system of claim 19, wherein the controller is shaped for placement around a patient's ear.

28. The system of claim 19, wherein the controller is configured to:
identify an implant having a unique ID tag;
communicate with the implant having the unique ID tag; and
send a signal to a transponder located in the implant.

29. The system of claim 19, wherein the controller is configured to:
provide an RF signal to the implant;
sense and record data; and
interface with a programming device.

30. The system of claim 19, wherein the controller is configured to communicate with the implant at preprogrammed intervals.

31. The system of claim 19, wherein the implant is configured to provide continuous open loop electrical stimulation to the HGN during sleep hours.

32. The system of claim 19, wherein the implant is configured to deliver multiple modes of stimulation.

33. The system of claim 19, wherein the implant is configured to provide stimulation in multiple dimensions.

34. The system of claim 19, wherein the neural interface does not include external wires or leads.

35. The system of claim 19, wherein the neural interface is configured to stimulate the HGN.

36. The system of claim 19, wherein the neural interface is configured to sense neural activity of the nerve it interfaces with and transmit that sensed neural activity to the core subsystem.

* * * * *